(12) United States Patent
Ishimaru et al.

(10) Patent No.: US 8,496,890 B2
(45) Date of Patent: Jul. 30, 2013

(54) PRETREATMENT APPARATUS FOR CHEMICAL ANALYSIS

(75) Inventors: Hirotoshi Ishimaru, Hitachinaka (JP); Hajime Kato, Tsuchiura (JP); Yasuhiko Sasaki, Tsuchiura (JP); Shinichi Fukuzono, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 1223 days.

(21) Appl. No.: 11/624,302

(22) Filed: Jan. 18, 2007

(65) Prior Publication Data
US 2007/0178017 A1 Aug. 2, 2007

(30) Foreign Application Priority Data
Jan. 30, 2006 (JP) .................... 2006-019960

(51) Int. Cl.
*B01L 3/00* (2006.01)

(52) U.S. Cl.
USPC ........... 422/552; 422/502; 422/504; 422/505; 422/547; 422/551

(58) Field of Classification Search
USPC ............... 422/99, 100, 101, 102, 502, 504, 422/505, 547, 551, 552; 435/288.3, 288.4, 435/288.5
See application file for complete search history.

(56) References Cited

U.S. PATENT DOCUMENTS

| 4,557,600 A | 12/1985 | Klose et al. |
| 5,863,502 A * | 1/1999 | Southgate et al. ............ 422/417 |
| 6,416,642 B1 * | 7/2002 | Alajoki et al. ................ 204/451 |
| 2004/0018116 A1 * | 1/2004 | Desmond et al. .............. 422/58 |
| 2006/0063273 A1 | 3/2006 | Asogawa et al. |

FOREIGN PATENT DOCUMENTS

| JP | 58-47260 | 3/1983 |
| JP | 3-255956 | 11/1991 |
| JP | 10-170495 | 6/1998 |
| JP | 2001-527220 | 12/2001 |
| JP | 2004-184138 | 7/2004 |
| JP | 2004-301715 | 10/2004 |
| JP | 2005-330272 | 12/2005 |
| JP | 2005-345160 | 12/2005 |
| WO | WO 99/33559 | 7/1999 |

OTHER PUBLICATIONS

JP Search Report of Appln. No. 2006-019960 dated Jan. 18, 2011.

* cited by examiner

*Primary Examiner* — Jill Warden
*Assistant Examiner* — Dwayne K Handy
(74) *Attorney, Agent, or Firm* — Antonelli, Terry, Stout & Kraus, LLP.

(57) ABSTRACT

In a pretreatment apparatus for transferring and mixing a specimen liquid and a reagent in a reagent reservoir, comprising containers for holding the specimen liquid and the reagent, flow paths connecting the containers in series, and a dialysis flow path including a dialysis membrane facing to the flow path, the mixing is brought about by transferring the liquid from the containers to the flow paths and a return by stoppage of transferring the liquid, and subsequently the liquid is made flow into the dialysis flow path.

4 Claims, 13 Drawing Sheets

PRETREATMENT APPARATUS FOR CHEMICAL ANALYSIS

BACKGROUND OF THE INVENTION

The present invention relates to a pretreatment apparatus for chemical analysis, in which apparatus a specimen liquid and a reagent or the like are transferred and mixed with each other, and an inhibitory substance is removed therefrom, particularly preferable for fragmentating protein in the specimen of protein to analyze a performance of the protein.

It is known and disclosed by, for example, JP-A-2004-301715 that for obtaining a primary structure information from a specimen of protein, a pipette tip is filled with hydrophobic fine grain carriers including hydrophobic surfaces of organic polymer, silica, glass or the like, a solution of the specimen of protein is inhaled and discharged repeatedly by a solution handling robot to fix the protein to the hydrophobic fine grain carriers, and reagents previously contained in a well plate are inhaled and discharged to fragmentate the protein to obtain a primary structure of a peptide after fragmentation.

Further, JP-A-10-170495 (FIG. 6) discloses an analysis apparatus for assessing a quality of various kinds of liquid, in which a liquid passage is formed by a clearance between blocks, a stirring part and a mixing part are arranged on an analysis passage, and a reagent is supplied from a reagent passage through a flow regulating valve to the mixing part.

BRIEF SUMMARY OF THE INVENTION

According to the prior art disclosed by JP-A-2004-301715, an operator puts protein specimens into eppen tubes or the like, reagents are distributed among the eppen tubes or the like respectively to generate respective reactions in processes, the specimens after the reaction are transferred into respective dialysis containers including dialysis membranes, and the specimens after the dialysis are brought back to the eppen tubes or the like to fragmentate a protein with catabolic enzyme, so that a necessary time period for fragmentating the protein in the protein specimen is elongated. Further, by a handling robot for transferring the specimen, a size of the apparatus is great, and a mechanism thereof is complicated so that a periodic maintenance is necessary.

Further, in JP-A-10-170495, the flow regulating valve, a check valve and so forth need to be arranged in the blocks, it is difficult for a liquid of trace quantity such as some to dozens micro-liters to be handled, so that a correctness in gathering an amount of the liquid and adjusting a dilution thereof is not obtainable, and there is a probability of a contamination of the specimen (particularly an interfusion of fugus, that is, interfusion and growth of microbe in pure culture caused by unidentified agents) and a leakage.

An object of the present invention is to solve a problem of the above prior art by realizing an application to various purposes, various kinds of specimen and the liquid of trace quantity, a pretreatment of good correctness, repeatability and reliability, particularly an automatic continuous treatment in franmentation of the protein in the specimen of protein applicable to an analysis for primary structures of various proteins.

According to the invention for solving the above problem, a pretreatment apparatus for transferring and mixing a specimen liquid and a reagent contained in containers in a reagent reservoir, comprises flow paths connecting the containers in series, and a dialysis flow path including a dialysis membrane between the flow paths, wherein a mixing is brought about by transferring the liquid from the containers to the flow paths and a return by stoppage of transferring the liquid, and subsequently the liquid is made flow into the dialysis flow path.

According to the invention, since the containers and the dialysis flow path including the dialysis membrane are connected in series in the reagent reservoir, pretreatments for chemical analysis are integrated for the continuous treatment in high reliability for the pretreatment protocol for the various purposes, various kinds of specimen and the liquid of trace quantity.

Other objects, features and advantages of the invention will become apparent from the following description of the embodiments of the invention taken in conjunction with the accompanying drawings.

DETAILED DESCRIPTION OF THE INVENTION

In a field of performance analysis for protein, a need of systematic performance analysis for extracellular or intracellular protein, or protein formed artificially by cell strain or cell-free system, increases. For the performance analysis for protein, a primary structure of the protein needs to be analyzed firstly, and the protein needs to be fragmentated to become peptide for the analysis, but since the protein includes variation actually, it cannot be changed uniformly to the peptide.

Therefore, a pretreatment is performed before chemical analysis for detecting a substance or determining a chemical composition, and a protocol of pretreatment before mass spectrography of a generic protein includes necessarily a denaturation/reduction process, an alkylation process, a demineralization process and an enzyme digestion process. That is, a denaturation reagent and a reduction reagent are supplied into a specimen including the protein to be stirred to form an intermediate product A, an alkylation agent is supplied into the intermediate product A to be stirred to form a dialysis specimen, and the dialysis specimen is demineralized to form an intermediate product B. Finally, an enzyme is supplied into the intermediate product B to perform an enzyme digestion of the protein to form a final product. The final product is a specimen to be analyzed by a mass spectrometer.

Figure 1:
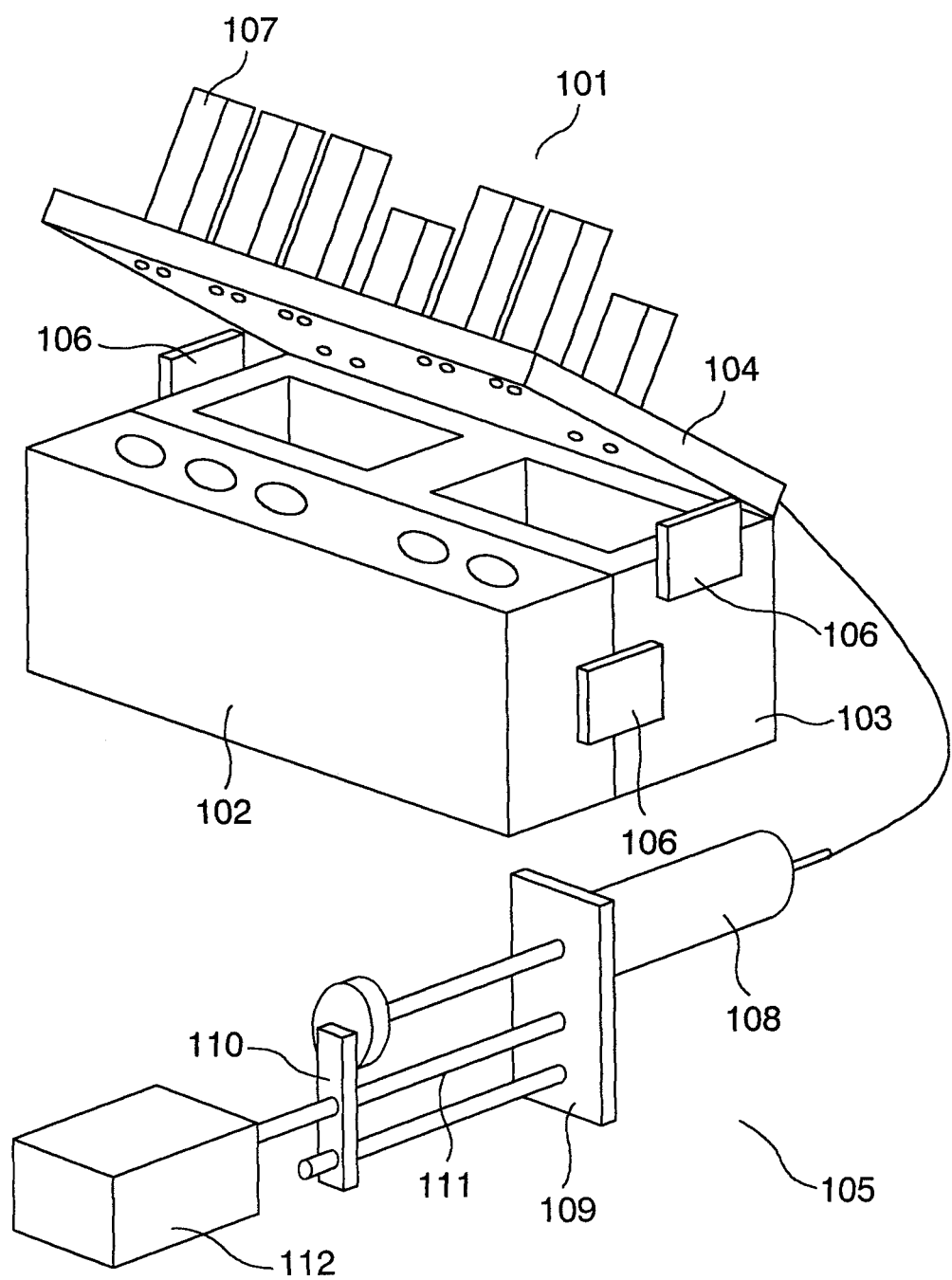
FIG. 1 is an oblique projection view of a pretreatment apparatus for chemical analysis as an embodiment of the invention.

FIG. 1 shows schematically a pretreatment apparatus for chemical analysis as an embodiment.

A pretreatment apparatus for chemical analysis 101 includes a reagent reservoir 102 including a plurality of containers for holding a specimen and a reagent and a dialysis path, a dialysis buffer container 103 for holding a dialysis buffer, an air-line manifold 104 for feeding the specimen and the reagent, and a syringe pump 105 as a pressure source. Further, the reagent reservoir 102, the dialysis buffer container 103 and the air-line manifold 104 are fixed to each other by a fixing jig 106 so that they are detachable with respect to each other and their passages are sealed at joints therebetween.

A liquid feed system includes the air-line manifold 104 having electromagnetic valves 107, a syringe 108, a cylinder fixing member 109, a support plate 110 for driving a piston, a drive shaft 111 for moving the support plate 110, and a motor 112 as a drive source.

Figure 2:
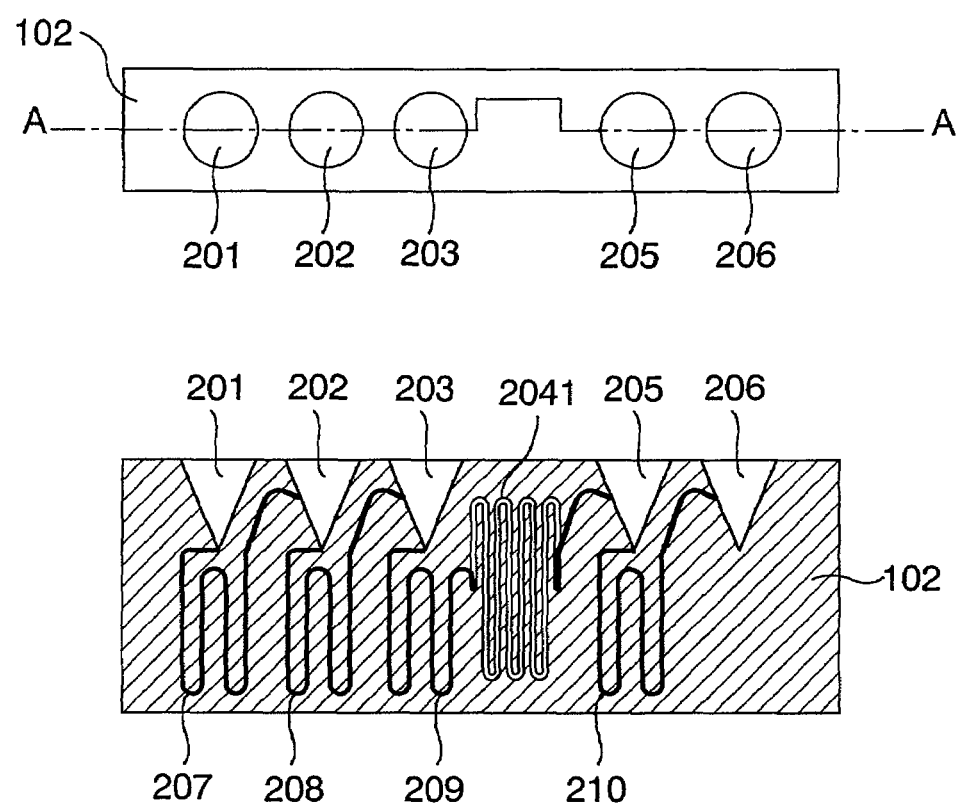
FIG. 2 is a combination of upper and cross sectional views of a reagent reservoir of the embodiment.

An upper part of FIG. 2 is an upper view of the reagent reservoir 102, and a lower part thereof is A-A cross sectional view. The reagent reservoir 102 has a specimen holding container 201 for holding a specimen, a reduction container 202 for holding a reduction reagent to perform the reduction of the specimen, an alkylation container 203 for holding an alkylation reagent to perform the alkylation of the specimen, a specimen side dialysis path 2041, an enzyme digestion container 205 for holding an enzyme to perform an enzyme digestion, and a specimen receiving container 206 for receiving and holding the specimen after the enzyme digestion. These containers are connected in series by liquid feed paths 207, 208, 209 and 210.

Figure 3:
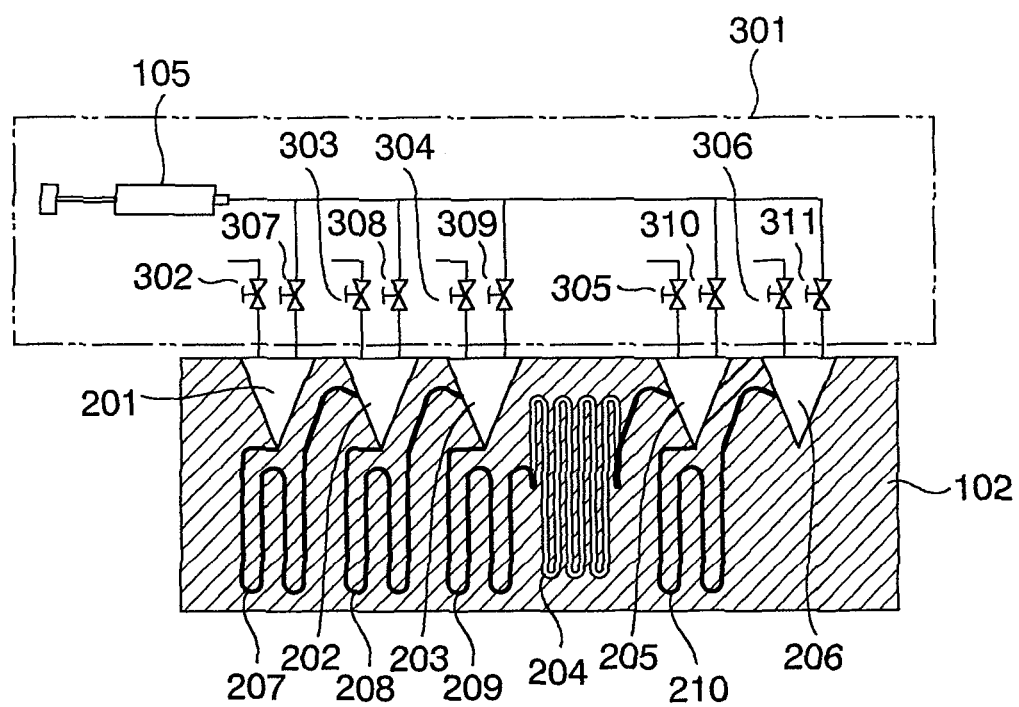
FIG. 3 is a schematic view of a liquid transfer system of the embodiment.

FIG. 3 includes A-A cross sectional view of the reagent reservoir 102 in FIG. 2, and a schematic view of a liquid feed system 301 detachably mounted on the reagent reservoir 102 with a pressure seal therebetween. The liquid feed system 301 has the syringe pump 105, electromagnetic valves 302, 303, 304, 305 and 306 for releasing pressures in the respective containers to the atmosphere, and electromagnetic valves 307, 308, 309, 310 and 311 for applying the pressure from the syringe pump 105.

When the liquid is fed from the specimen holding container 201 to the reduction container 202, the electromagnetic valve 307 connected to the specimen holding container 201 to be pressurized and the electromagnetic valve 303 connected to the reduction container 202 to be released to the atmosphere are opened, and the syringe pump 105 is driven. The liquid flows from a bottom of the specimen holding container 201 through the liquid feed flow path 207 into the reduction container 202. After completion of feeding the liquid, the syringe pump 105 is stopped, and both of the electromagnetic valves 303 and 307 are closed. Subsequently, the electromagnetic valves 308 and 304 are opened and the syringe pump 105 are driven to feed the liquid to the alkylation container 203. After completion of feeding the liquid, the syringe pump 105 is stopped, and both of the electromagnetic valves 304 and 308 are closed.

When the liquid is fed to the enzyme digesting container 205, the electromagnetic valves 309 and 305 are opened and the syringe pump 105 is driven. After completion of feeding the liquid, the syringe pump 105 is stopped, and both of the electromagnetic valves 305 and 309 are closed. Finally, the electromagnetic valves 310 and 306 are opened and the syringe pump 105 are driven to feed the liquid to the liquid receiving container 206.

After completion of feeding the liquid to the liquid receiving container 206, the syringe pump 105 is stopped, and both of the electromagnetic valves 306 and 310 are closed. That is, when the liquid is fed from the container to the subsequent container, the electromagnetic valve connected to the container to be pressurized and the electromagnetic valve connected to the subsequent container released to the atmosphere are opened, and the syringe pump is driven so that the liquid feed from the container to the subsequent container is performed. After completion of feeding the liquid, the syringe pump and both of the electromagnetic valves 306 and 310 are deenergized. Since a residual pressure in the air-line manifold 104 and the reagent reservoir 102 affects a liquid holding force, the syringe pump 105, the electromagnetic valve for supplying the pressure and the electromagnetic valve for releasing to the atmosphere may be deenergized simultaneously, but it is preferable for secure operation that they are deenergized in a sequential order from the syringe pump 105 through the electromagnetic valve for supplying the pressure to the electromagnetic valve for releasing to the atmosphere.

Basic factors for performing the protocol for the pretreatment are feeding the liquid of micro-liters or dozens microliters, mixing the liquids and a dialysis of the specimen with a dialysis membrane, and a shape of the containers of the reagent reservoir 102 is explained.

Figure 4:
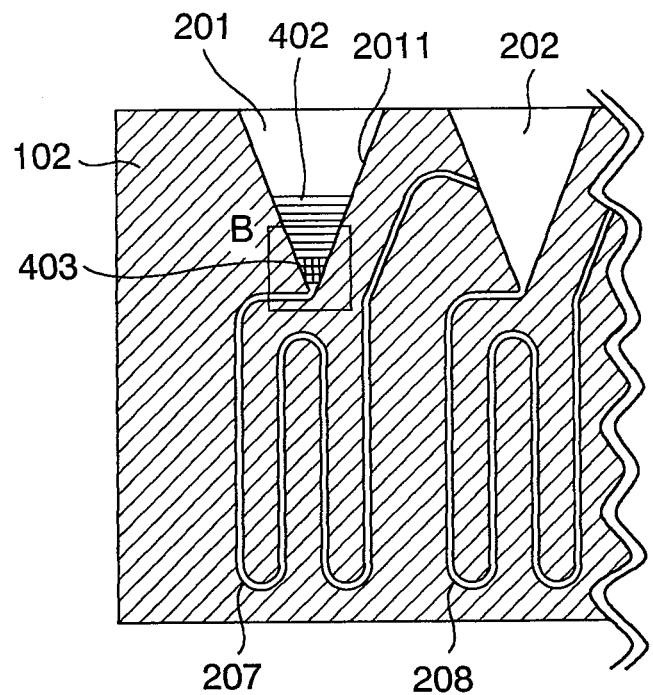
FIG. 4 is a combination of cross sectional views of a substantial part of the reagent reservoir of the embodiment.
Figure 4:
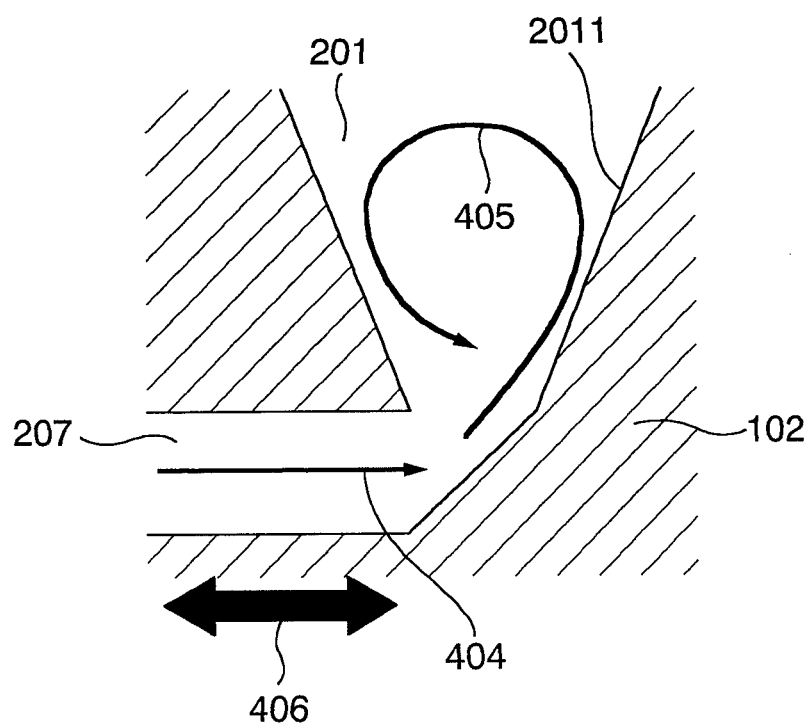

An upper view of FIG. 4 is a A-A cross sectional view of a substantial part of the reagent reservoir 102 in FIG. 2, in which upper view each of the containers arranged in the reagent reservoir 102 has a cross section decreasing in a direction toward a downstream side (bottom of the container), and the liquid feed flow paths 207 and 208 are connected to the deepest bottom of the container. The liquid feed flow paths 207 and 208 are connected substantially perpendicularly to a container wall surface 2011. It is preferable for making an amount of the residual liquid during the feed of the liquid as small as possible that cross sections of the liquid feed flow paths 207 and 208 are circular. Incidentally, when a rate of recovering the liquid is permitted to be low or the cross section of the liquid feed flow path is extremely small while an aspect ratio thereof is close to 1 and the pressure source can exclude a flow resistance of the liquid feed flow path during the feed of the liquid, the cross section of the liquid feed flow path may be rectangular while preventing the liquid from remaining.

Volumes of the liquid feed flow paths 207 and 208 are sufficient for transferring and holding at least a part of the specimen. The liquid feed flow path between the container and the subsequent container windles in two dimension to decrease a space for receiving it, but may be spiral or windle in three dimension while keeping similar liquid feed. Further, a diameter of each of the liquid feed flow paths is sufficiently small for securely keeping a differential pressure or a fluidal sealing with a viscosity and/or surface tension of the liquid of the specimen and so forth between the containers.

Next, a mixture between two of the liquids will be explained. A lower part of FIG. 4 is an enlarged view of a region B in an upper part of FIG. 4. That is, the upper part of FIG. 4 is an enlarged view of a joint between the liquid feed flow path 207 and a bottom of the specimen holding container 201 arranged in the reagent reservoir 102. As shown in the drawings, the container holds the solution A 402 and the solution B 403 to be mixed with each other, the whole or a part of the two solutions are fed into the liquid feed flow path 207, the feed is stopped, and the solutions are fed backward toward the specimen hold container 201 in a direction shown by an arrow 404. Accordingly the flow from the liquid feed flow path 207 into the specimen hold container 201 impinges on a container wall surface 2011 to deflect the flow as shown by an arrow 405 at the bottom of the container so that the two liquids of extremely small quantity are mixed efficiently and securely. Further, after the whole or part of the two solutions are brought back from the liquid feed flow path 207 into the container temporarily, the solutions are fed back and forth repeatedly to facilitate the mixture of the two solutions.

Incidentally, the liquid feed flow path 207 is connected to the container wall surface 2011 perpendicularly, and the greater an instreaming angle from the liquid feed flow path 207 into the specimen hold container 201 is, the higher a mixing efficiency is.

Figure 5:
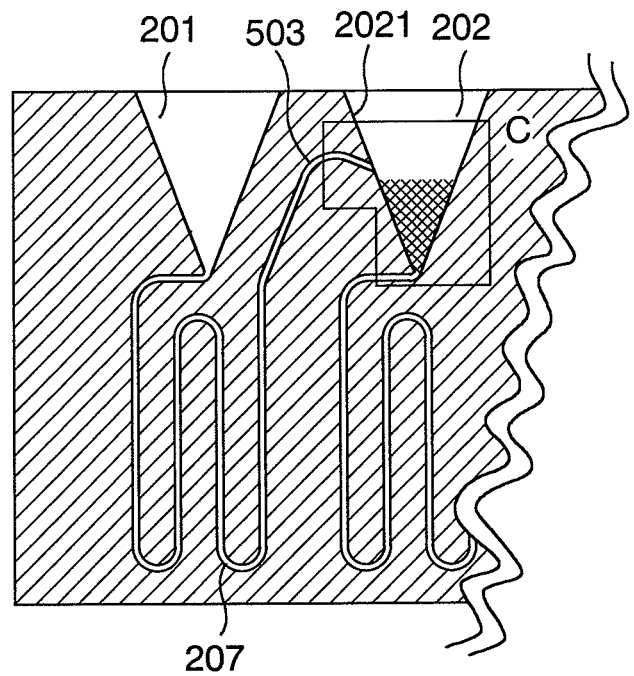
FIG. 5 is a combination of cross sectional views of another substantial part of the reagent reservoir of the embodiment.
Figure 5:
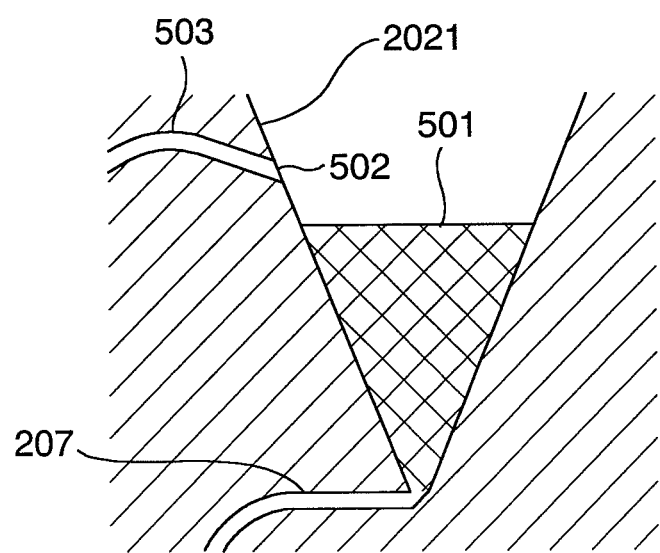

Next, a connection from the liquid feed flow path 207 to a reduction container 202 will be explained. An upper part of FIG. 5 is a cross sectional view of A-A substantial part of the reagent reservoir 102 shown in the upper part of FIG. 2. A lower part of FIG. 5 is an enlarged view of a region C. A connection portion 502 between the liquid feed flow path 207 and the reduction container 202 is arranged above a surface 501 of the liquid received in the reduction container 202. By this arrangement of the connection portion between the liquid feed flow path 207 and the reduction container 202, a reverse flow of the specimen caused by capillary phenomenon is prevented, and a contamination of the specimen and a decrease in collecting rate of the solution are restrained. The connection direction of the liquid feed flow path 207 is vertically downward with respect to the container so that the liquid fed from the specimen hold container 201 is received by a bottom of the reduction container 202. Incidentally, it is preferable for its connecting angle to the container to be along the container wall surface 2011, but a bending angle of a bent portion 503 of the flow path at a upstream side from the connection portion 502 needs to be an acute angle for obtaining such connecting angle to increase a pressure loss, whereby preferably the bending angle of the bent portion 503 is not the acute angle.

Figure 6:
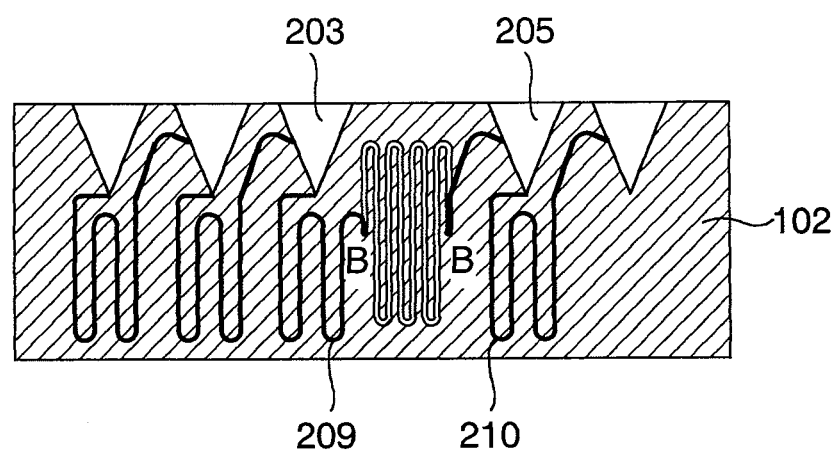
FIG. 6 is a combination of cross sectional views of the dialysis flow path of the embodiment.
Figure 6:
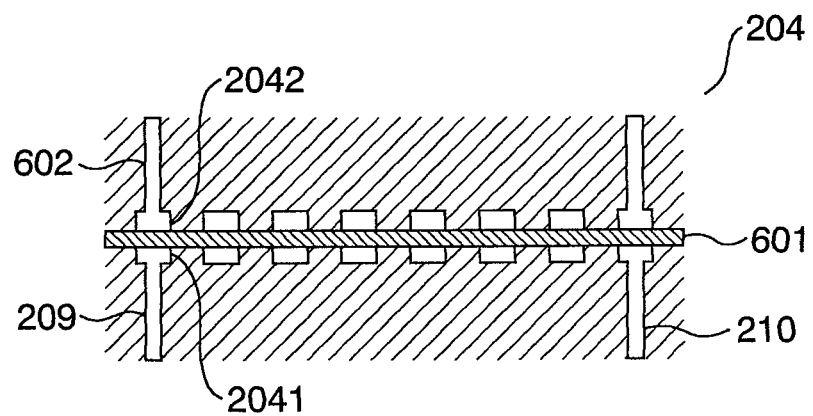
Figure 7:
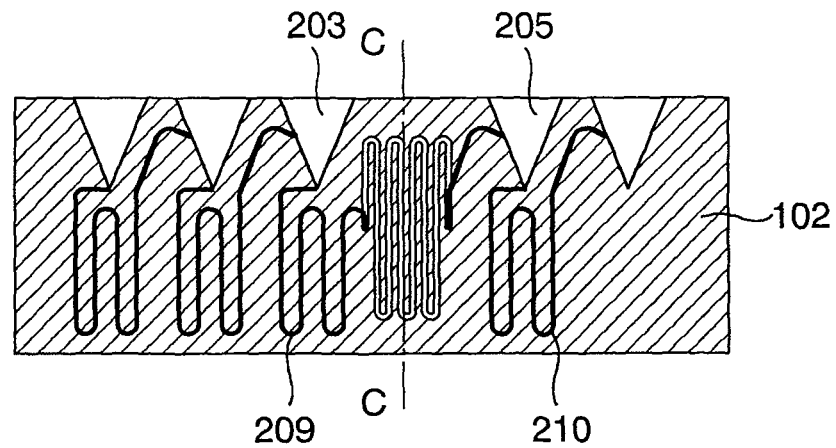
FIG. 7 is a combination of cross sectional views of the dialysis flow path of the embodiment as seen in another direction.
Figure 7:
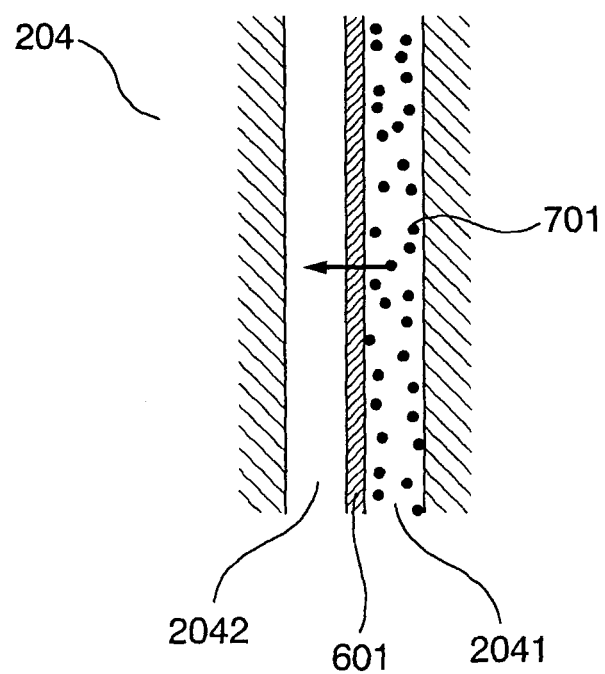

Next, a dialysis of the specimen by use of a dialysis membrane will be explained. Upper parts of FIGS. 6 and 7 are A-A cross sectional views of the specimen reservoir 102 shown in the upper part of FIG. 2. A lower part of FIG. 6 is a B-B cross sectional view of the substantial part. A lower part of FIG. 7 is a C-C cross sectional view of the substantial part.

A pretreatment protocol for the specimen includes a demineralization process for removing salt from the specimen to perform an enzyme digestion. That is, a dialysis flow path 204 of micro flow path is arranged between an alkylation container 203 and an enzyme digestion container 205 in the reagent reservoir 102 so that a continuous treatment of the pretreatment protocol for chemical analysis is performed and a speeding up of the demineralization process is obtained.

The dialysis flow path 204 is arranged along a dialysis membrane 601 through which a dialysis flow path of specimen side 2041 and a dialysis flow path of dialysis buffer side 2042 face to each other. The flow path 209 is connected to the dialysis flow path of specimen side 2041 and the dialysis flow path of dialysis buffer side 2042 so that the specimen and the dialysis buffer flows perpendicularly to the dialysis flow path of specimen side 2041 and the dialysis flow path of dialysis buffer side 2042. The specimen flows from the alkylation container 203 through the flow path 209 into the dialysis flow path of specimen side 2041 to be held thereby. On the other hand, the dialysis buffer flows from a dialysis buffer container 103 through a flow path 602 into the dialysis flow path of dialysis buffer side 2042 to be held thereby. A contact between the liquids through the dialysis membrane 601 is kept as shown in the lower part of FIG. 7, and the salt 701 is transferred from the specimen into the dialysis buffer by a concentration gradient of salt in the vicinity of the dialysis membrane 601.

A pretreatment protocol for mass spectrography for general protein performed by the pretreatment apparatus for chemical analysis 101 will be explained.

Figure 8:
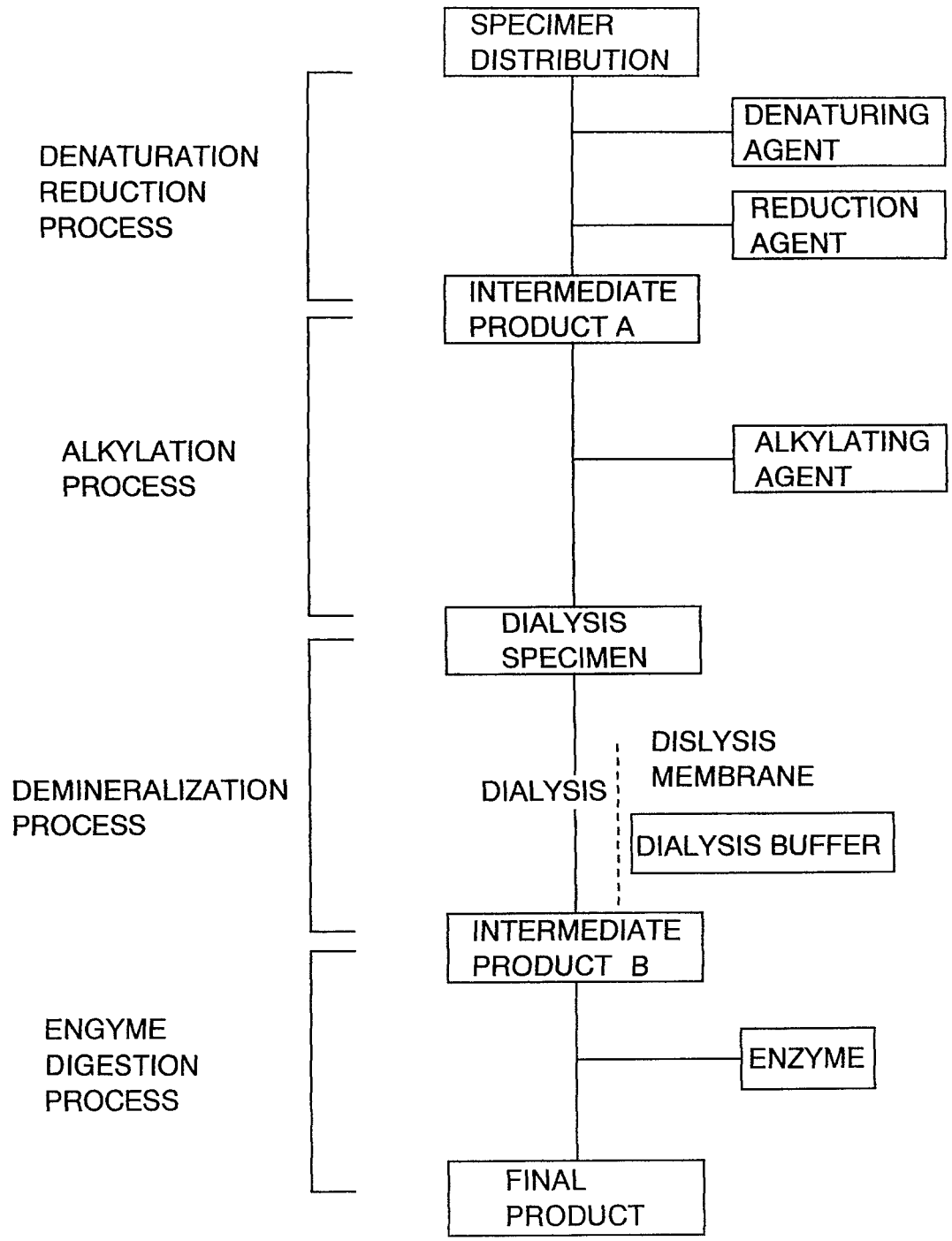
FIG. 8 is a flow chart of protocol of pretreatment for protein mass spectrometry.

FIG. 8 shows the pretreatment protocol for mass spectrography for general protein, and the pretreatment protocol includes the denaturation/reduction process, the alkylation process, the demineralization process and the enzyme digestion process. That is, the denaturation reagent and the reduction reagent are applied to the specimen including the protein, and subsequently they are mixed to each other to form the intermediate product A. The alkylation reagent is applied to the intermediate product A, and they are mixed to each other to a dialysis specimen. Subsequently, the dialysis specimen and the dialysis buffer are made contact each other through the dialysis membrane 601 to remove the salt 701 from the specimen so that the intermediate product B is formed. Finally, the enzyme is applied to the intermediate product B to perform the enzyme digestion of the protein so that the final product is formed. The final product is a specimen to be analyzed by a mass spectrograph.

An example for performing the protocol when the pretreatment apparatus for chemical analysis is used, will be explained.

Figure 9:
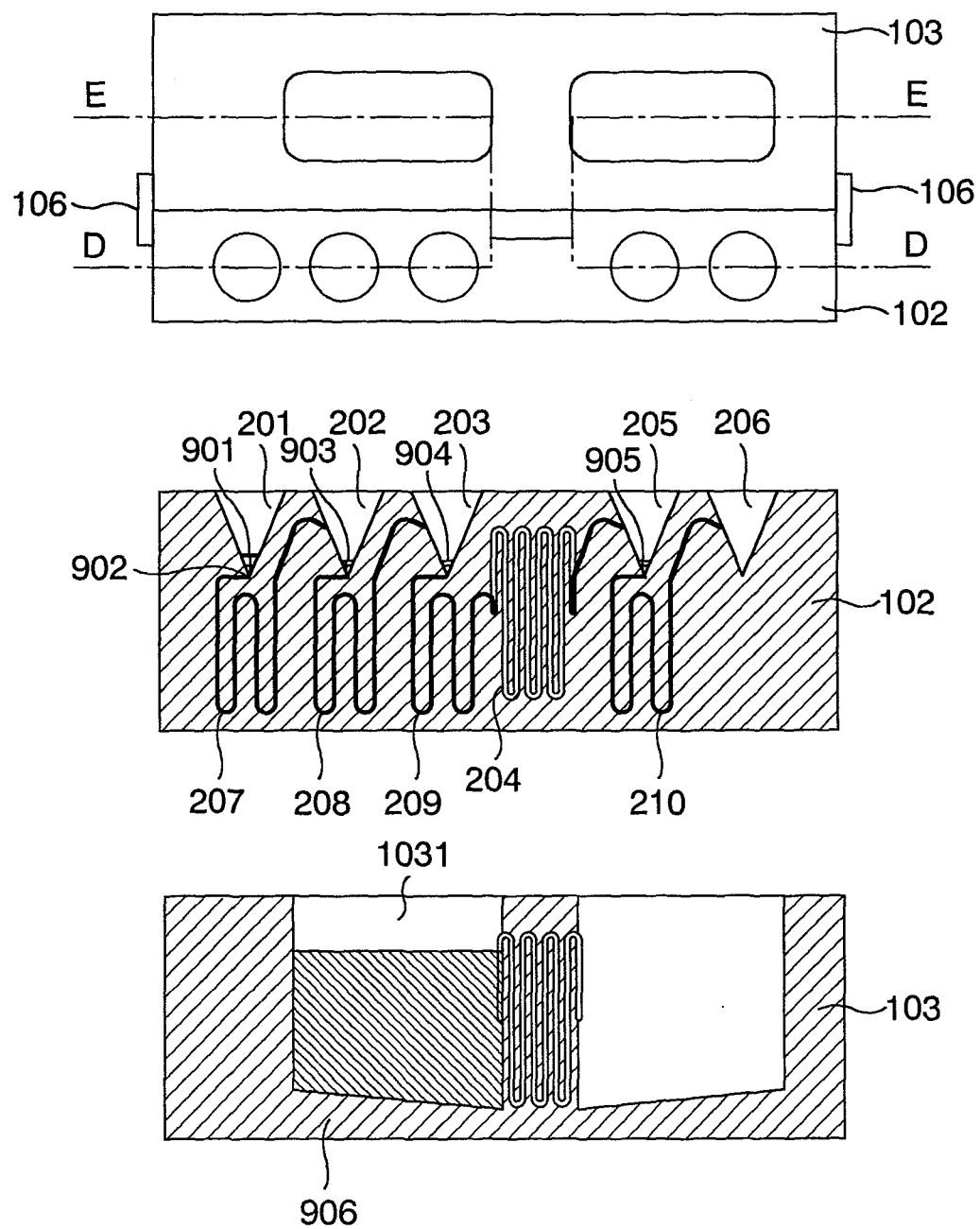
FIG. 9 is a combination of upper view of the reagent reservoir of the embodiment, and cross sectional views of substantial parts of the embodiment.

An upper part of FIG. 9 is an upper view of a combination of the specimen reservoir 102 and the dialysis buffer container 103. A middle part of FIG. 9 is a D-D cross sectional view, and a lower part thereof is an E-E cross sectional view. FIGS. 10, 11, 12, 13, 14 and 15 are D-D cross sectional views and E-E cross sectional views corresponding to respective steps of the protocol.

As shown in the middle part of FIG. 9, at first, the specimen of protein 901 and the denaturation reagent 902 are supplied into the specimen container 201 in the reagent reservoir 102. The reduction reagent 903 is supplied into the reduction container 202 to be held therein, the alkylation reagent 904 is supplied into the alkylation container 203 to be held therein, the enzyme 905 is supplied into the enzyme digestion container 205 to be held therein, and the dialysis buffer 906 is supplied into the dialysis buffer hold container 1031 to be held therein. Subsequently, the air line manifold 104 (not shown) is mounted on the reagent reservoir 102 and the dialysis buffer container 103.

The air line manifold 104 is detachably attached to the reagent reservoir 102 and the dialysis buffer container 103 by a fixing jig 106 to keep sealing against pressures from the containers. Incidentally, supplying the specimen, the reagents and so forth after an assembly of the apparatus are automatically performed, and operations of the electromagnetic valves and drive of the syringe pump are controlled by PC with recorded program.

Figure 10:
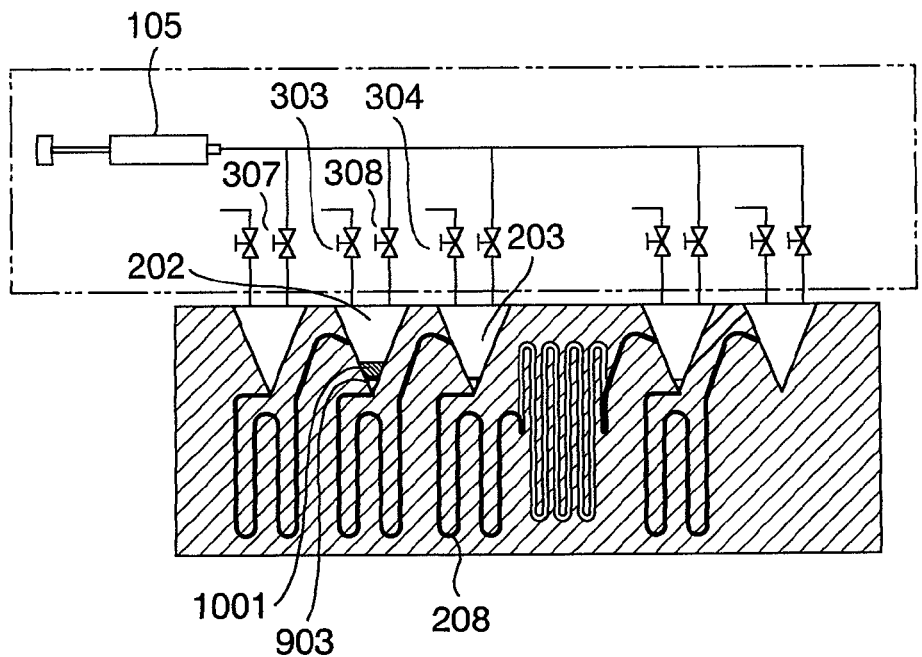
FIG. 10 is a block view for explaining a pretreatment process of the embodiment.

In the denaturation/reduction process of the protocol, the electromagnetic valves 303 and 307 are opened and the syringe pump is driven to urge a gaseous matter into the specimen hold container 201 to feed the protein specimen 901 and the denaturation reagent 902 from the specimen hold container 201 into the flow path 207 to be held temporarily therein. Subsequently, the syringe pump 105 and the electromagnetic valves 303 and 307 are deenergized. Subsequently, the electromagnetic valves 303 and 307 are opened and the syringe pump is driven to suck the gaseous matter from the specimen hold container to bring back the protein specimen 901 and the denaturation reagent 902 from the flow path 207 into the specimen hold container 201. Subsequently, the syringe pump 105 and the electromagnetic valves 303 and 307 are deenergized. The electromagnetic valves 303 and 307 are reopened and the syringe pump is driven to feed the protein specimen 1001 after the denaturation from the specimen hold container 201 into the reduction container 2002 (FIG. 10).

The continuous feed of the liquid is generated by a difference in pressure between the container and the subsequent container so that no influence is applied to the containers for holding the alkylation reagent 904, the dialysis buffer 906 and the enzyme 905 to be kept in the respective containers.

The electromagnetic valves 304 and 308 are opened and the syringe pump is driven to feed the protein specimen 1001 after the denaturation and the reduction reagent 903 into the flow path 208 to be held temporarily therein. Subsequently, the syringe pump 105 and the electromagnetic valves 304 and 308 are deenergized. Subsequently, the electromagnetic valves 304 and 308 are opened and the syringe pump 105 is driven to bring back the protein specimen 1001 after the denaturation and the reduction reagent 903 into the reduction container 202. During this time, the intermediate product A 1101 is formed. The syringe pump 105 and the electromagnetic valves 303 and 307 are deenergized.

Figure 11:
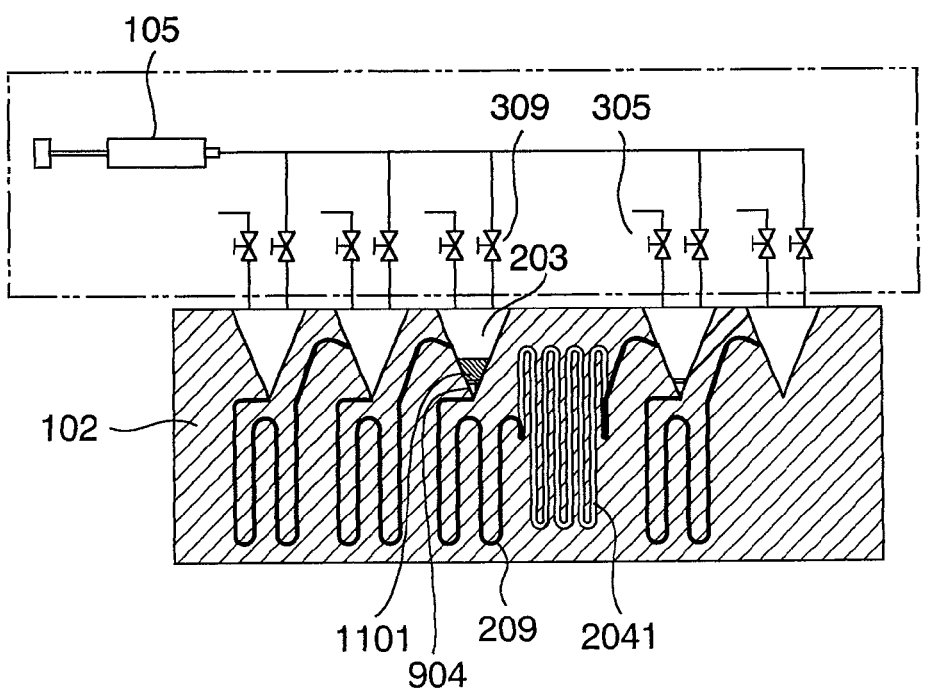
FIG. 11 is a block view for explaining a pretreatment process of the embodiment.

The electromagnetic valves 304 and 308 are reopened and the syringe pump 105 is driven to feed the intermediate product A 1101 into the alkylation container 203 (FIG. 11). Subsequently, the syringe pump 105 and the electromagnetic valves 304 and 308 are deenergized.

Figure 12:
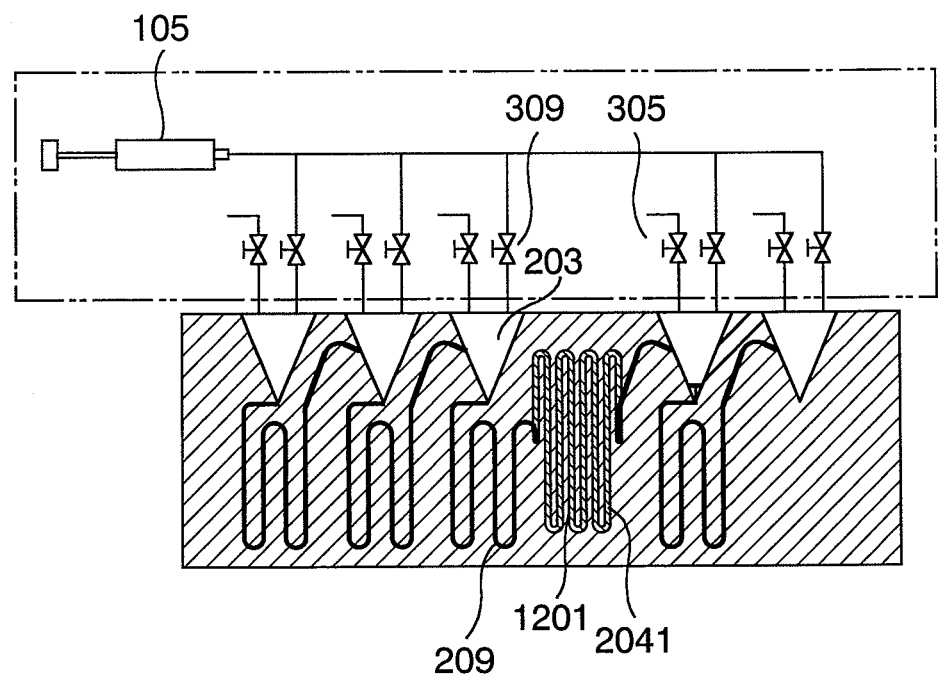
FIG. 12 is a block view for explaining a pretreatment process of the embodiment.

The electromagnetic valves 309 and 305 are opened and the syringe pump 105 is driven to feed the intermediate product A 1101 and the alkylation reagent 904 from the alkylation container 203 into the flow path 209 to be held temporarily therein. Subsequently, the syringe pump 105 and the electromagnetic valves 305 and 309 are deenergized. Subsequently, the electromagnetic valves 305 and 309 are opened and the syringe pump 105 is driven to bring back the intermediate product A 1101 and the alkylation reagent 904 into the alkylation container 203. During this time, the dialysis specimen 1201 is formed. The electromagnetic valves 309 and 305 are opened and the syringe pump 105 is driven to feed the dialysis specimen 1201 into the specimen side dialysis path 2041 to be held temporarily (FIG. 12). Subsequently, the syringe pump 105 and the electromagnetic valves 305 and 309 are deenergized.

Figure 13:
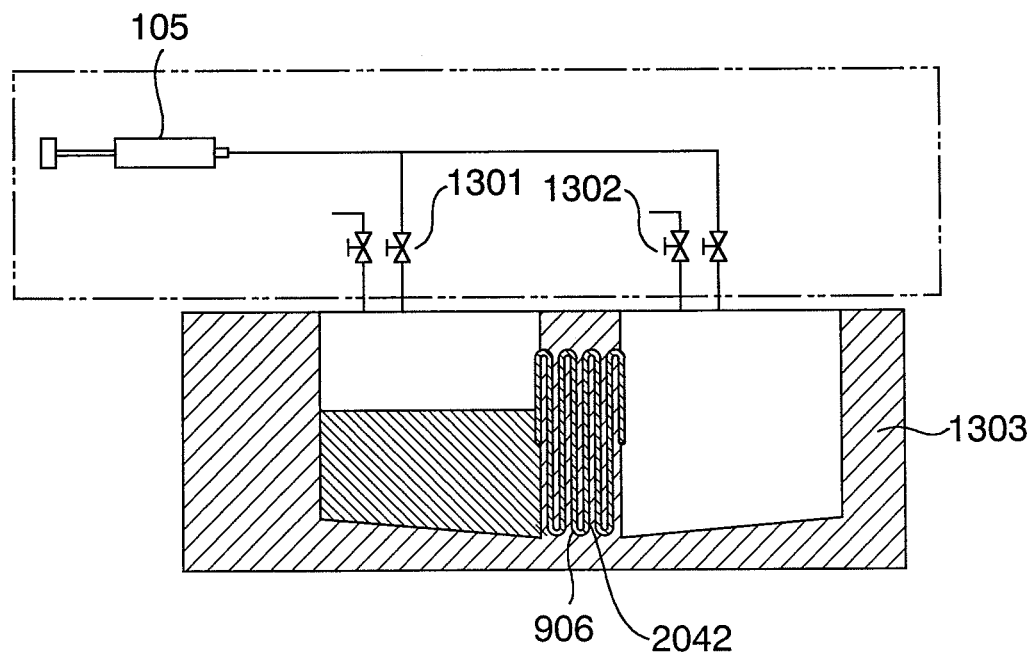
FIG. 13 is a block view for explaining a pretreatment process of the embodiment.

Subsequently, as shown in FIG. 13, the electromagnetic valves 1301 and 1302 are opened and the syringe pump 105 is driven to feed the dialysis buffer 906 into the dialysis flow path of dialysis buffer side 2042 to be held temporarily (FIG. 13). The syringe pump 105 and the electromagnetic valves 1301 and 1302 are deenergized. By keeping this condition, the salt 701 is removed from the dialysis specimen 1201. In accordance with a time elapse, a salt concentration gradient in the vicinity of the dialysis membrane becomes even to decrease a dialysis efficiency. Therefore, in response to a predetermined time elapse, the electromagnetic valves 1301 and 1302 are opened and the syringe pump 105 is driven to discharge the dialysis buffer 906 of high salt concentration into the dialysis buffer collecting container 1303 and supply the fresh dialysis buffer 906 into the dialysis flow path of dialysis buffer side 2042.

The dialysis specimen 1201 is held in the specimen side dialysis path 2041 while the dialysis buffer 906 is held in the dialysis flow path of dialysis buffer side 2042. The syringe pump 105 and the electromagnetic valves 1301 and 1302 are deenergized. Until the demineralization of the protein specimen is completed, such process is repeated. By exchanging the dialysis buffer 906 at each elapse of predetermined time, the salt concentration gradient in the vicinity of the dialysis membrane is kept high to perform the demineralization efficiently. Alternatively, by feeding the dialysis buffer 906 continuously with a flow rate corresponding to a diffusion rate of the salt 701, the demineralization can be performed efficiently. After the completion of the demineralization, the intermediate product B 1401 is formed.

Figure 14:
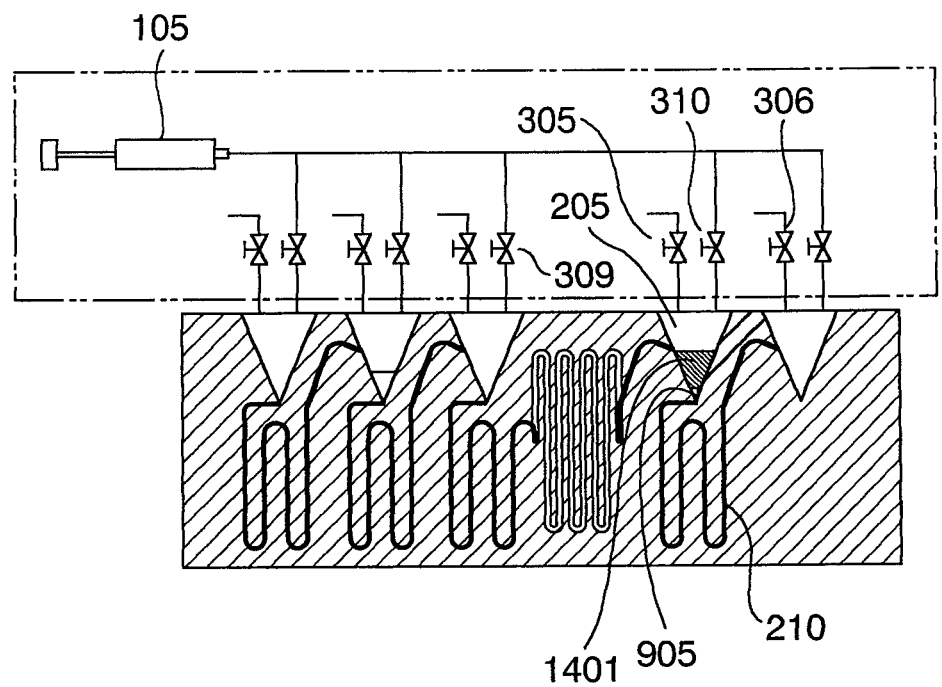
FIG. 14 is a block view for explaining a pretreatment process of the embodiment.
Figure 15:
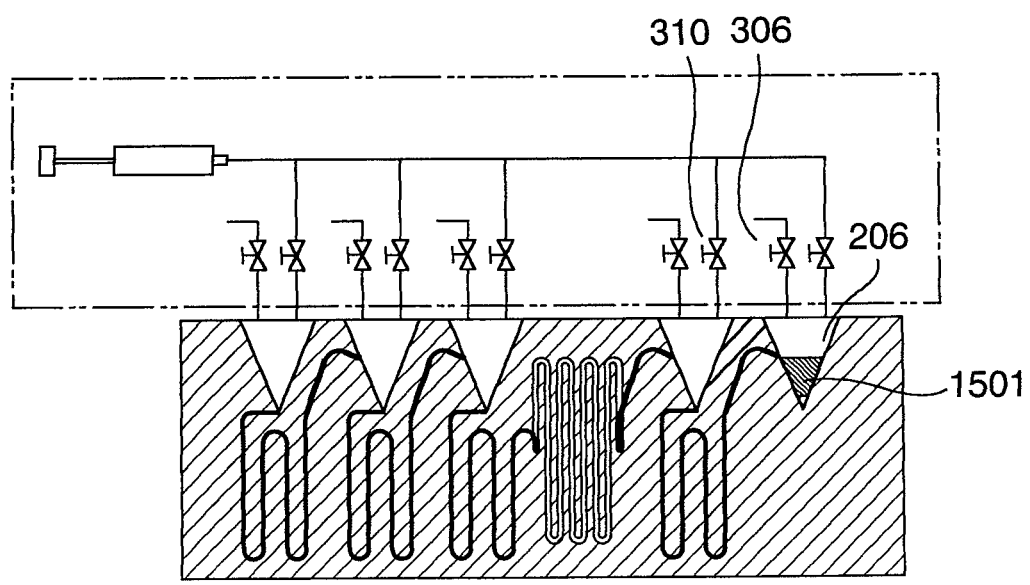
FIG. 15 is a block view for explaining a pretreatment process of the embodiment.

Subsequently, the electromagnetic valves 309 and 305 are opened and the syringe pump 105 is driven to feed the intermediate product B 1401 into the enzyme digestion container 205 (FIG. 14). The syringe pump 105 and the electromagnetic valves 305 and 309 are deenergized. The electromagnetic valves 305 and 309 are opened and the syringe pump 105 is driven to feed the intermediate product B 1401 and the enzyme 905 into the flow path 210 to be held temporarily. The syringe pump 105 and the electromagnetic valves 305 and 309 are deenergized. The electromagnetic valves 305 and 309 are opened and the syringe pump 105 is driven to bring back the intermediate product B 1401 and the enzyme 905 from the flow path 210 into the enzyme digestion container 205. During such time, the final product 1501 is formed. The syringe pump 105 and the electromagnetic valves 305 and 309 are deenergized. Finally, the electromagnetic valves 306 and 310 are opened and the syringe pump 105 is driven to feed the final product 1501 into the specimen receiving container 206 (FIG. 15). The final product 1501 is a specimen after the completion of the pretreatment protocol.

Incidentally, when a temperature control is required in each process of the pretreatment protocol, a temperature controlled heat source such as a heat block (not shown) may be arranged in the vicinity of each of the containers in the reagent reservoir 102. Further, when a desired temperature as a target of control is low, the whole of the apparatus may be set in a furnace to perform the pretreatment protocol. Materials of the reagent reservoir 102, the dialysis buffer container 103 and the air line manifold 104 may be any material capable of preventing nonspecific adhesion of the protein or the like. For example, it may be polycarbonate or polypropylene usable for eppen tip or the like.

Figure 16:
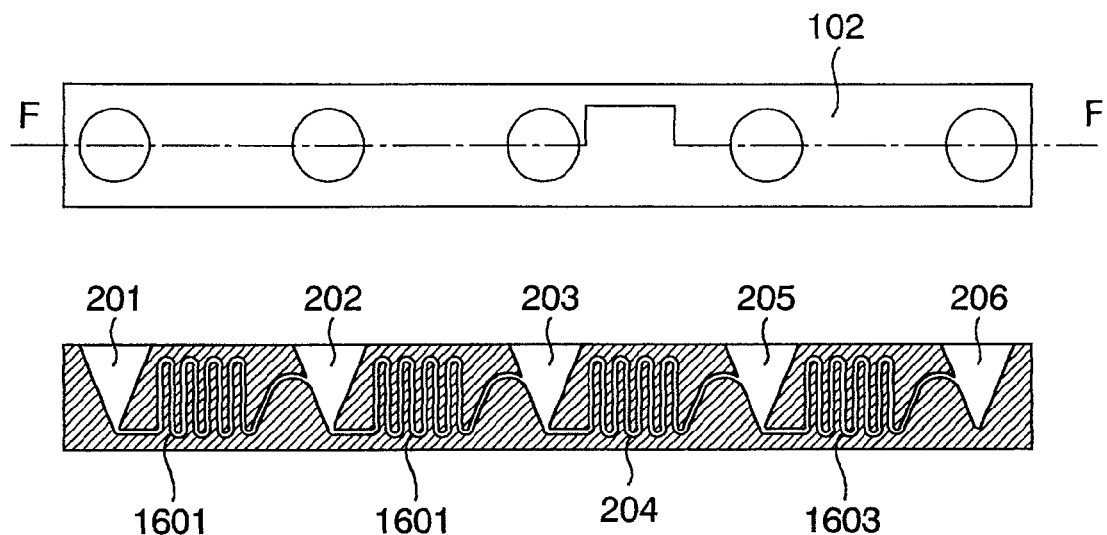
FIG. 16 is a combination of upper and cross sectional views of the reagent reservoir as another embodiment.

An upper part of FIG. 16 is an upper view of a second embodiment of the reagent reservoir 102, and a lower part thereof is F-F cross sectional view. The flow paths 207, 208, 209 and 210 do not need to be arranged below the containers, but flow paths 1601, 1602 and 1603 may be arranged at a same height as the containers while keeping the performance of the pretreatment unchanged.

Figure 17:
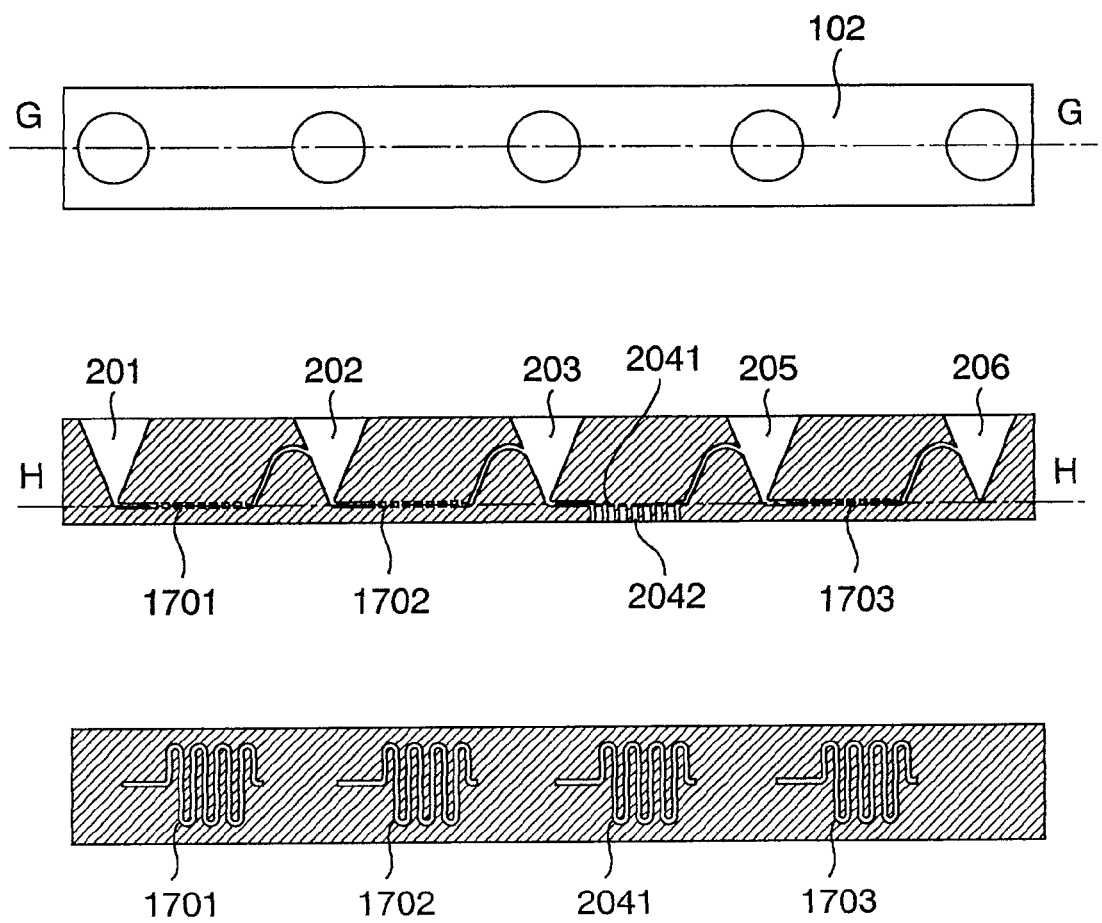
FIG. 17 is a combination of upper and cross sectional views of the reagent reservoir as another embodiment.

An upper part of FIG. 17 is an upper view of a third embodiment of the reagent reservoir 102, a middle part thereof is G-G cross sectional view and a lower part thereof is H-H cross sectional view. Flow paths 1701, 1702, 1703 and 2041 of the reagent reservoir 102 do not need to windle vertically, bur may windle horizontally. In the above second and third embodiments, the reagent reservoir 102 may be further miniaturized.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. A pretreatment apparatus for chemical analysis, comprising a plurality of containers which are arranged in a row, each of such plurality of containers being capable of containing one of a specimen liquid and a reagent, flow paths connecting the containers in series, a dialysis flow path including a dialysis membrane facing to the flow path, a syringe pump, first valves connected to respective ones of the containers and configured to release the respective containers to the atmosphere, and second valves operably connected to the syringe pump and respective ones of the containers and configured to supply a pressure from the syringe pump to the respective containers, wherein the containers have respective cross sections decreasing downward, an end of the flow path is connected to a bottom of a first one of the containers while another end of the flow path is connected to a container wall surface of a subsequent second one of the containers at a position higher than a liquid level in the second one of the containers with a downward direction, and the flow path has a volume sufficient for receiving therein temporarily at least a part of the liquid to be contained in each of the containers.

2. The pretreatment apparatus according to claim 1, wherein the row is formed by the first one of the containers as a specimen hold container for holding the specimen, the second one of the containers as a reduction container for holding the reagent for reduction, subsequent third one of the containers as an alkylation container for holding the reagent for alkylation, subsequent fourth one of the containers as an enzyme digestion container for holding the reagent of enzyme, and subsequent fifth one of the containers as a specimen receiving container for receiving the specimen after the enzyme digestion, and the dialysis flow path is arranged between the third and fourth ones of the containers as a part of the row.

3. The pretreatment apparatus according to claim 1, wherein each of the plurality of containers is operably connected to a respective one of the first valves and a respective one of the second valves.

4. The pretreatment apparatus according to claim 1, wherein a demineralization is performed in the dialysis flow path.

* * * * *